United States Patent
Yang

(10) Patent No.: US 11,304,615 B2
(45) Date of Patent: Apr. 19, 2022

(54) BIOLOGICAL FEATURE DETECTION APPARATUS AND ELECTRONIC TERMINAL

(71) Applicant: SHENZHEN GOODIX TECHNOLOGY CO., LTD., Shenzhen (CN)

(72) Inventor: Wangwang Yang, Shenzhen (CN)

(73) Assignee: SHENZHEN GOODIX TECHNOLOGY CO., LTD., Shenzhen (CN)

( * ) Notice: Subject to any disclaimer, the term of this patent is extended or adjusted under 35 U.S.C. 154(b) by 396 days.

(21) Appl. No.: 16/151,314

(22) Filed: Oct. 3, 2018

(65) Prior Publication Data

US 2019/0029544 A1    Jan. 31, 2019

Related U.S. Application Data

(63) Continuation of application No. PCT/CN2018/093807, filed on Jun. 29, 2018, which
(Continued)

(51) Int. Cl.
*A61B 5/1455* (2006.01)
*A61B 5/024* (2006.01)
*A61B 5/00* (2006.01)

(52) U.S. Cl.
CPC ...... *A61B 5/02427* (2013.01); *A61B 5/02416* (2013.01); *A61B 5/6803* (2013.01);
(Continued)

(58) Field of Classification Search
CPC .............. A61B 5/1455; A61B 5/14551; A61B 5/14552; A61B 5/6803; A61B 5/6817;
(Continued)

(56) References Cited

U.S. PATENT DOCUMENTS 3,471,348 A    10/1969 Shaheen et al.
6,078,829 A    6/2000 Uchida et al.
(Continued)

FOREIGN PATENT DOCUMENTS

CN    101897583    12/2010
CN    202446094    9/2012
(Continued)

OTHER PUBLICATIONS

Mendelson Y et al.: "Noninvasive Pulse Oximetry Utilizing Skin Reflectance Photoplethysmography", IEEE Transactions on Biomedical Engineering, IEEE Service Center, Piscataway, NJ, USA, vol. 35, No. 10, Oct. 1, 1988, pp. 798-805, XP002164422, ISSN: 0018-9294, DOI: 10.1109/10.7286 Section III.A; Figures 1-2.

*Primary Examiner* — Eric F Winakur
(74) *Attorney, Agent, or Firm* — Emerson, Thomson & Bennett, LLC; Roger D. Emerson; Warren A. Rosborough

(57) ABSTRACT

Embodiments of the present application provide a biological feature detection apparatus. The detection apparatus includes: a light emitting unit and a light receiving unit. The light emitting unit is configured to emit light to a detection surface of a biological tissue, the light emitted by the light emitting unit being processed by the biological tissue and then transmitted to the light receiving unit, the light receiving unit is configured to receive the light and perform a photoelectric conversion to generate an original electrical signal for biological feature detection, and at least one of the adjustable relative position and relative angle is defined between the light emitting unit and the light receiving unit. As such, accurate monitoring of the biological feature is achieved.

17 Claims, 10 Drawing Sheets

Related U.S. Application Data is a continuation of application No. PCT/CN2017/091042, filed on Jun. 30, 2017.

(52) U.S. Cl.
CPC ........ *A61B 5/6817* (2013.01); *A61B 5/14551* (2013.01); *A61B 2562/164* (2013.01); *A61B 2562/166* (2013.01)

(58) Field of Classification Search
CPC .. A61B 5/02427; A61B 5/6815; A61B 5/6816
See application file for complete search history.

(56) References Cited

U.S. PATENT DOCUMENTS

| | | | |
|---|---|---|---|
| 7,245,953 B1 * | 7/2007 | Parker | A61B 5/14552 600/310 |
| 8,233,955 B2 * | 7/2012 | Al-Ali | A61B 5/14552 600/344 |
| 8,405,999 B2 | 3/2013 | Takahashi | |
| 2014/0180039 A1 | 6/2014 | LeBoeuf et al. | |
| 2014/0235967 A1 | 8/2014 | LeBoeuf et al. | |
| 2015/0182135 A1 | 7/2015 | Ma et al. | |
| 2015/0208933 A1 | 7/2015 | Satomi et al. | |
| 2016/0367144 A1 | 12/2016 | Matsuo | |

FOREIGN PATENT DOCUMENTS

| | | |
|---|---|---|
| CN | 202699147 U | 1/2013 |
| CN | 103491860 | 1/2014 |
| CN | 203539358 U | 4/2014 |
| CN | 103845063 | 6/2014 |
| CN | 105379306 | 3/2016 |
| CN | 205181356 U | 4/2016 |
| CN | 205458634 | 8/2016 |
| CN | 105997026 A | 10/2016 |
| CN | 106308776 | 1/2017 |
| CN | 106344042 | 1/2017 |
| CN | 106527105 | 3/2017 |
| CN | 106793956 | 5/2017 |

* cited by examiner

BIOLOGICAL FEATURE DETECTION APPARATUS AND ELECTRONIC TERMINAL

CROSS-REFERENCE TO RELATED APPLICATIONS

The present application is a continuation of international application No. PCT/CN2018/093807, filed on Jun. 29, 2018, which claims priority to the international application No. PCT/CN2017/091042, filed on Jun. 30, 2017, both are hereby incorporated by reference in its entireties.

TECHNICAL FIELD

Embodiments of the present application relate to the technical field of biological feature detection, and in particular, relate to a biological feature detection apparatus and an electronic terminal.

BACKGROUND

Rapid development of smart devices, for example, emergence of smart phones, smart bracelets, smart earphones and the like, facilitates practice of applications having a healthcare function, for example, detection of heart rate, blood oxygen and the like biological features. Specifically, these smart devices are used in scenarios of monitoring the heart rate and blood oxygen during exercise or movement to judge whether the biological feature of a user is normal, or monitoring the heart rate and blood oxygen during sleeping to judge whether the biological feature of a user is normal.

With regard to the practice of the above applications having the healthcare function, the current commonly used manner is: measuring the biological feature based on the optical theory, for example, the light reflection theory and the light projection theory. Using the light reflection theory as an example, the light emitted by a light emitter is incident to the biological tissue and then reflected by the biological tissue, and a light receiver receives the reflected light and performs biological feature detection based on the reflected light. During this process, the incident light is reflected under effects (absorption and diffusion) of the blood in the tissue and then the reflected light is formed. Since the blood in the tissue may be periodically changed, the biological feature may be obtained by sensing and analyzing the reflected light. Analogously, with respect to the light projection theory, the biological feature may be obtained by sensing and analyzing the projected light.

In the prior art, using biological feature detection practiced based on the light reflection theory as an example, the relative position between the light emitter and the light receiver is generally constant. Therefore, accurate monitoring of the biological feature may not be achieved by adjusting the relative position between the light emitter and the light receiver.

SUMMARY

Embodiments of the present application are intended to provide a biological feature detection apparatus and an electronic terminal, to at least solve the above technical problem in the prior art.

To achieve the objective of embodiments of the present application, embodiments of the present application provide a biological feature detection apparatus. The detection apparatus includes: a light emitting unit and a light receiving unit. The light emitting unit is configured to emit light to a detection surface of a biological tissue, the light emitted by the light emitting unit being processed by the biological tissue and then transmitted to the light receiving unit, the light receiving unit is configured to receive the light and perform a photoelectric conversion to generate an original electrical signal for biological feature detection, and at least one of an adjustable relative position and relative angle is defined between the light emitting unit and the light receiving unit.

Optionally, in an embodiment of the present application, the light emitting unit is arranged on a first substrate, and the light receiving unit is arranged on a second substrate.

Optionally, in an embodiment of the present application, the detection apparatus further includes: a flexible member. The flexible member is connected to the first substrate and the second substrate respectively via a solder pad or a plug, such that at least one of the adjustable relative position and relative angle is defined between the light emitting unit and the light receiving unit.

Optionally, in an embodiment of the present application, the first substrate and the second substrate have a multilayer structure; and correspondingly, the detection apparatus further comprises: a flexible member. At least one end of the flexible member is embedded into the multilayer structures of the first substrate and/or the second substrate to be connected to the first substrate and/or the second substrate respectively, such that at least one of the adjustable relative position and relative angle is defined between the light emitting unit and the light receiving unit.

Optionally, in an embodiment of the present application, the first substrate and the second substrate have a multilayer structure. Any layer in the multilayer structure of the first substrate is made of a flexible material and extends outside to the second substrate and connected to any layer in the multilayer structure of the second substrate; or any layer in the multilayer structure of the second substrate is made of a flexible material and extends outside to the first substrate and connected to any layer in the multilayer structure of the first substrate, such that at least one of the adjustable relative position and relative angle is defined between the light emitting unit and the light receiving unit.

Optionally, in an embodiment of the present application, the apparatus further includes: an optical shielding unit, configured to shield or absorb the light emitted by the light emitting unit to prevent the light emitted by the light emitting light from being directly transmitted to the light receiving unit without being processed by the biological tissue. The apparatus MAY further include a light guiding unit that is configured to guide the light emitted by the light emitting unit to the detection surface of the biological tissue, and/or configured to guide the light being processed by the biological tissue to the light receiving unit.

Optionally, in an embodiment of the present application, the optical shielding unit and the light guiding unit are integrally arranged, or the optical shielding unit and the light guiding unit are separately arranged.

Optionally, in an embodiment of the present application, the light emitting unit and the light receiving unit are both provided with the light guiding unit. The light guiding unit on the light emitting unit and the light guiding unit on the light receiving unit are integrally arranged or separately arranged.

Optionally, in any embodiment of the present application, a surface shape of the light guiding unit and/or the optical shielding unit matches a shape of the detection surface of the biological tissue.

Optionally, in an embodiment of the present application, the apparatus further includes: a processing circuit, wherein the processing circuit is configured to perform an analog-to-digital conversion for the original electrical signal to form a digital signal and filters the digital signal; and/or further comprising a control circuit, wherein the control circuit is configured to control the light emitting unit to emit light to the biological tissue.

Optionally, in an embodiment of the present application, the apparatus further includes: a processor; wherein the processor is configured to perform biological feature detection according to the original electrical signal.

Optionally, in an embodiment of the present application, the relative position is a linear distance between a geometric center of the light emitting unit and a geometric center of the light receiving unit, and the relative angle is a normal angle between a planar surface of the light emitting unit and a planar surface of the light receiving unit.

Optionally, in an embodiment of the present application, the biological feature is a heart rate feature and a blood oxygen feature based on a photoplethysmogram signal.

Optionally, in an embodiment of the present application, the biological tissue is an ear, and during biological feature detection, the light receiving unit and/or the light emitting unit is attached to a tragus inner-side region of the ear; or the light receiving unit and/or the light emitting unit is attached to a region between an inferior crus of antihelix and a crus of helix of the ear; or the light receiving unit and/or the light emitting unit is attached to a region between an antihelix and a crus of helix of the ear; or the light receiving unit and/or the light emitting unit is attached to a cimba concha region of the ear; or the light receiving unit and/or the light emitting unit is attached to an earlobe region of the ear; or the light receiving unit and/or the light emitting unit is located in a concha cavity of the ear; or the light receiving unit and/or the light emitting unit is located in a region enclosed by the crus of helix, an ear canal entrance and the antihelix close to an antitragus of the ear.

Optionally, in an embodiment of the present application, when the light receiving unit is attached to the tragus inner-side region, the light emitting unit is located in an underneath connection region between an intertragic notch and an outer ear canal entrance; or the light emitting unit is attached to the tragus inner-side region, the light receiving unit is located in an underneath connection region between an intertragic notch and an outer ear canal entrance.

Optionally, in any embodiment of the present application, the apparatus further includes: a wearing assistance mechanism; wherein the light receiving unit and the light emitting unit are arranged on the wearing assistance mechanism, such that the light receiving unit and the light emitting unit is arranged in the region between the inferior crus of antihelix and the crus of helix or such that the light receiving unit and the light emitting unit is arranged in the region between the antihelix and the crus of helix.

Optionally, in any embodiment of the present application, the apparatus further includes: an elastic unit; wherein, during biological feature detection, the elastic unit is configured to enable the light emitting and the light receiving unit to be tightly attached to the biological tissue.

Embodiments of the present application further provide an electronic terminal. The electronic terminal includes the biological feature detection apparatus as described in any one of the above embodiments.

In the biological feature detection apparatus according to embodiments of the present application, the light emitting unit is configured to emit light to a detection surface of a biological tissue, the light emitted by the light emitting unit being processed by the biological tissue and then transmitted to the light receiving unit, the light receiving unit is configured to receive the light and perform a photoelectric conversion to generate an original electrical signal for biological feature detection, and at least one of the adjustable relative position and relative angle is defined between the light emitting unit and the light receiving unit. As such, accurate monitoring of the biological feature is achieved.

DETAILED DESCRIPTION

Practice of the present application is described in detail with reference to drawings and specific embodiments, such that the practice of addressing the technical problem using the technical means according to the present application and achieving the technical effects may be better understood and conducted.

In the biological feature detection apparatus according to embodiments of the present application, the light emitting unit is configured to emit light to a detection surface of a biological tissue, the light emitted by the light emitting unit being processed by the biological tissue and then transmitted to the light receiving unit, the light receiving unit is configured to receive the light and perform a photoelectric conversion to generate an original electrical signal for biological feature detection, and at least one of the adjustable relative position and relative angle is defined between the light emitting unit and the light receiving unit. As such, accurate monitoring of the biological feature is achieved.

Figure 1:
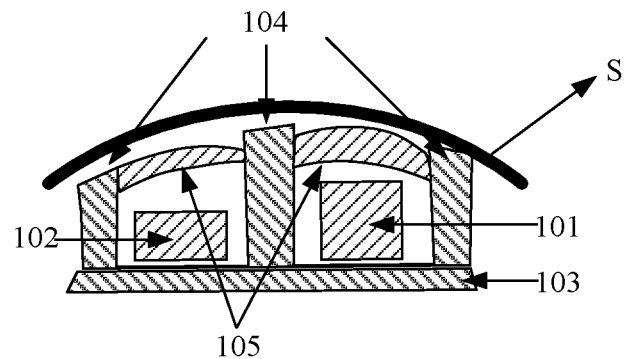
FIG. 1 is a schematic structural diagram of a biological feature detection apparatus according to the first embodiment of the present application.

FIG. 1 is a schematic structural diagram of a biological feature detection apparatus according to the first embodiment of the present application. In this embodiment, a biological feature detection apparatus 1 is also referred to as a biological feature detection apparatus. Specifically, the biological feature detection apparatus includes a light emitting unit 101 and a light receiving unit 102. The light emitting unit 101 is configured to emit light to a detection surface of a biological tissue, and the light receiving unit 102 is configured to receive the light and perform a photoelectric conversion to generate an original electrical signal for biological feature detection.

Optionally, in this embodiment, the biological feature detection apparatus may further include a hard substrate 103. The light emitting unit 101 and the light receiving unit 102 are both arranged on the hard substrate 103.

Optionally, in this embodiment, the biological feature detection apparatus may further include: an optical shielding unit 104, configured to shield or absorb the light emitted by the light emitting unit to prevent the light emitted by the light emitting light from being directly transmitted to the light receiving unit without being processed by the biological tissue, and hence to improve accuracy of biological feature detection.

Optionally, in this embodiment, the biological feature detection apparatus may further include: a light guiding unit 105, configured to guide the light emitted by the light emitting unit to the detection surface of the biological tissue, and/or configured to guide the light being processed by the biological tissue to the light receiving unit. Specifically, a light guiding unit 105 may be arranged on each of the light emitting unit 101 and the light receiving unit 102. That is, the biological feature detection apparatus includes two light guiding units 105. The two light guiding units 105 may be integrally arranged or separately arranged. That is, the light guiding unit 105 on the light emitting unit 101 and the light guiding unit 105 on the light receiving unit 102 may be integrally arranged or separately arranged. However, it should be noted that a light guiding unit 105 may also be arranged on either the light emitting unit 101 or the light receiving unit 102. That is, the biological feature detection apparatus includes one light guiding unit 105. In this embodiment, the light guiding unit 105 improves efficiency of light transmission, lowers entire power consumption of the apparatus and improves detection accuracy.

Specifically, when the optical shielding unit 104 and the light guiding unit 105 are both arranged on the biological feature detection apparatus, the optical shielding unit 104 and the light guiding unit 105 are integrally arranged, or the optical shielding unit 104 and the light guiding unit 105 are separately arranged.

In this embodiment, surfaces, facing toward the detection surface, of the light guiding unit 105 and the optical shielding unit 104 are defined to match with the detection surface of the biological tissue. If the detection surface is a planar surface, the surfaces, facing toward the detection surface, of the light guiding unit 105 and the optical shielding unit 104 are also planar surfaces; if the detection surface is an arc surface, the surfaces, facing toward the detection surface, of the light guiding unit 105 and the optical shielding unit 104 are also arc surfaces; and if the detection surface is an irregular surface, the surfaces, facing toward the detection surface, of the light guiding unit 105 and the optical shielding unit 104 are also irregular curved surfaces. It should be noted that the surface of the light guiding unit 105 or the optical shielding unit 104 that faces toward the detection surface, may be shaped to match the detection surface of the biological tissue according to the structure design needs.

In another embodiment, based on the embodiment illustrated in FIG. 1, the biological feature detection apparatus may further include a processing circuit. The processing circuit is configured to perform an analog-to-digital conversion for the original electrical signal to form a digital signal and filter the digital signal. The biological feature detection apparatus may further include a control circuit that is configured to control the light emitting unit to emit light to the biological tissue.

It should be noted that functionality of the processing circuit may be extended according to the actual needs, which is not limited to analog-to-digital conversion and filtration.

In another embodiment, based on the embodiment illustrated in FIG. 1, the biological feature detection apparatus may further include a processor. The processor is configured to perform biological feature detection according to the original electrical signal. During biological feature detection performed by the processor according to the original electrical signal, a biological feature signal may be specifically extracted from a digital signal experiencing analog-to-digital conversion and filter processing by the processing circuit; or the processor directly performs analog-to-digital conversion and filtering for the original electrical signal, and then performs biological feature detection. It should be noted that the processor may be an independently configured microprocessor, or may be the processor of the terminal connected to the earphone.

Figure 2:
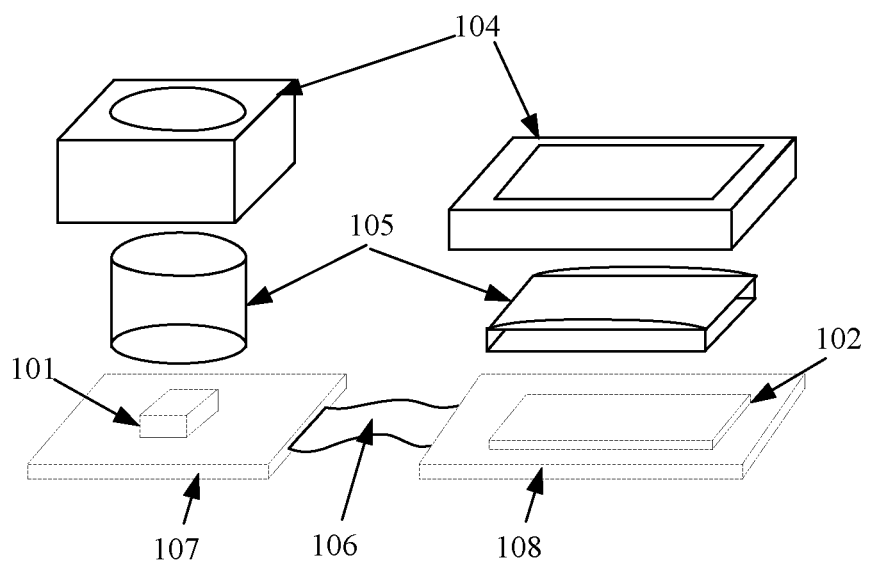
FIG. 2 is a schematic structural diagram of a biological feature detection apparatus according to the second embodiment of the present application.

FIG. 2 is a schematic structural diagram of a biological feature detection apparatus according to the second embodiment of the present application. As illustrated in FIG. 2, in this embodiment, using an exploded schematic diagram as an example, like the embodiment illustrated in FIG. 1, the biological feature detection apparatus likewise includes: a light emitting unit 101 and a light receiving unit 102. Different from the above embodiment, the biological feature detection apparatus further includes: a flexible member and two substrates. The two substrates are respectively a first substrate 107 and a second substrate 108. The light emitting unit 101 is arranged on the first substrate 107, and the light receiving unit 102 is arranged on the second substrate 108. In this embodiment, the first substrate 107 and the second substrate 108 are both hard substrates, and the flexible member 106 is a flexible circuit board. The hard substrate may be, for example, a PCB, a hybrid board of a FPC and a reinforcement board or the like structure that may not be bent; and the flexible circuit board may be, for example, an FPC, an FFC, a set of electrical connectors or the like structure that may be bent.

It should be noted that, alternatively, the light emitting unit 101 and the light receiving unit 102 may also be arranged on the same rigid substrate or flexible substrate.

In this embodiment, the light emitting unit 101 is approximately a columnar light source, and the light receiving unit 102 is approximately a planar array to receive the light with a greater light sensing area as much as possible.

In this embodiment, the light emitting unit 101 and the light receiving unit 102 are connected (including, but not limited to, physical connection and/or electrical connection) to each other via the flexible member 106. The flexible member is configured to adjust at least one of a relative position and relative angle between the light emitting unit 101 and the light receiving unit 102.

Optionally, in this embodiment, the relative position is a linear distance between a geometric center of the light emitting unit 101 and a geometric center of the light receiving unit 102, and/or the relative angle is a normal angle between an outer surface of the light emitting unit 101 and an outer surface of the light receiving unit 102.

Optionally, in any embodiment of the present application, a normal of the light receiving unit 102 facing towards an outer surface of the detection surface is parallel to a normal of the detection surface; and/or a normal of the light emitting unit 101 facing towards an outer surface of the detection surface is parallel to a normal of the detection surface.

It should be noted that, alternatively, either the first substrate or the second substrate is a flexible substrate, or the first substrate and the second substrate are both flexible substrates. Further, the flexible member may be a partial structure of the flexible substrate.

In another embodiment, the light emitting unit 101 and the light receiving unit 102 may be separately arranged from the processing circuit in terms of physical aspect, or may be integrally arranged with the processing circuit, the control circuit and the processor.

In another embodiment, the light emitting unit 101, the light receiving unit 102, the processing circuit and the MCU are physically separate structures, or may be integrated to form a chip structure.

In another embodiment, the biological feature detection apparatus may include a plurality of light emitting units and one light receiving unit, to improve emission efficiency of light.

In another embodiment, the biological feature detection apparatus may include a plurality of light receiving units and one light emitting unit, to improve reception efficiency of light.

In the above embodiment including the flexible member, due to presence of the flexible member, the relative position and the relative angle between the light emitting unit and the light receiving unit may be randomly adjusted, such that the biological feature detection apparatus is suitable for the detection surface having any shape, and quality of the original electrical signal is improved.

In addition, when the embodiment illustrated in FIG. 2 is applied to the specific product of the earphone, the adjustability of the relative position and the relative angle between the light emitting unit and the light receiving unit enables the entire earphone product to have a relatively compact structure.

Figure 3:
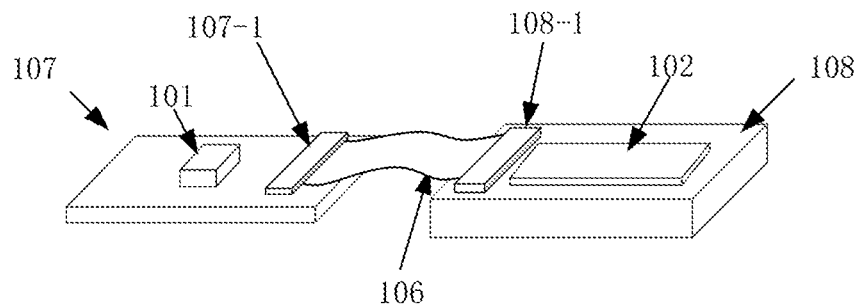
FIG. 3 is a schematic structural diagram of a biological feature detection apparatus according to the third embodiment of the present application.

FIG. 3 is a schematic structural diagram of a biological feature detection apparatus according to the third embodiment of the present application. As illustrated in FIG. 3, this embodiment emphasizes the connection of the flexible member in FIG. 2 to the first substrate and the second substrate in FIG. 2 as an independent structure member.

In this embodiment, with respect to the light emitting unit 101 and the light receiving unit 102, a driving circuit and a detecting circuit need to be respectively configured. During circuit design, the driving circuit and the detecting circuit are generally integrated in a control chip. The control chip, as an entirety, may be disposed on the side of the first substrate 107 where the light emitting unit 101 is arranged or the side of the second substrate 108 where the light receiving unit 102 is arranged. As such, the detecting circuit of the light receiving unit 102 and the light receiving unit 102 may not be arranged on the same substrate, that is, the second substrate 108; or the driving circuit of the light emitting unit 101 and the light emitting unit 101 may not be arranged on the same substrate, that is, the first substrate 107. Considering that the detecting circuit of the light receiving unit 102 and the light receiving unit 102 may not be arranged on the same substrate or the driving circuit of the light emitting unit 101 and the light emitting unit 101 may not be arranged on the same substrate, in this embodiment, since the flexible member 106 is an independent structure member that is absolutely independent of the first substrate and the second substrate, and electrical connection lines are configured, during connection to the first substrate and the second substrate, the light receiving unit 102 and the detecting circuit thereof, or the light emitting unit 101 and the driving circuit thereof are ensured to collaboratively work. For example, if the light receiving unit 102 and the detecting circuit thereof are not arranged on the same substrate, the detecting circuit and the light receiving unit 102 may communicate with each other via the electrical connection lines in the flexible member 106. Therefore, the flexible member 106 is connected to the first substrate and the second substrate respectively via a first plug 107-1 and a second plug 108-1, and at least one of the adjustable relative position and relative angle is defined between the light emitting unit and the light receiving unit.

In another embodiment, the first plug 107-1 and the second plug 108-1 may also be replaced by a solder pad.

Figure 4:
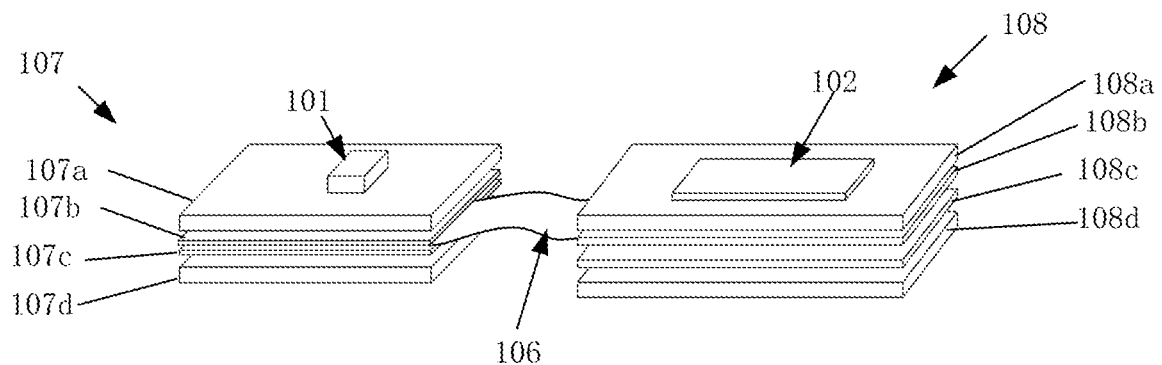
FIG. 4 is a schematic structural diagram of a biological feature detection apparatus according to the fourth embodiment of the present application.

FIG. 4 is a schematic structural diagram of a biological feature detection apparatus according to the fourth embodiment of the present application. Different from the embodiment as illustrated in FIG. 2 or FIG. 3, the first substrate 107 and the second substrate 108 have a multilayer structure. Two ends of the flexible member are respectively embedded into the multilayer structures of the first substrate and the second substrate to be respectively connected to the first substrate and the second substrate. For example, since the structure of the flexible member is a double-layer structure made of a flexible material, and two up-down adjacent layers in the multilayer structures of the first substrate and the second substrate is made of a flexible material (that is, the first substrate and the second substrate are flexible-hard hybrid boards), during manufacture, the two ends of the flexible member 106 are directly interconnected to the two adjacent layers made of the flexible material in the first substrate and the second substrate, and are laminated with the other layers in the first substrate. In addition, for practice of the electrical connection, a region where the flexible member is laminated with the other layers is provided with a via to practice the electrical connection, which is equivalent to replacement of the plug or the solder pad.

In this embodiment, the case where the first substrate 107 and the second substrate 108 are each a PCB having a four-layer structure is used as an example. Specifically, the first substrate 107 includes four layers from top to bottom: a first layer PCB 107a, a second layer PCB 107b, a third layer PCB 107c and a fourth layer PCB 107d; and the second substrate 108 includes four layers from top to bottom: a first layer PCB 108a, a second layer PCB 108b, a third layer PCB 108c and a fourth layer PCB 108d.

Specifically, the second layer PCB 107b and the third layer PCB 107c correspond to the double-layer structure in the flexible member 106. Therefore, one end of the flexible member 106 is sandwiched between the first layer PCB 107a and the fourth PCB 107d in the first substrate 107. Likewise, the other end of the flexible member 106 is sandwiched between the first layer PCB 108a and the fourth PCB 108d in the second substrate 108.

Figure 5:
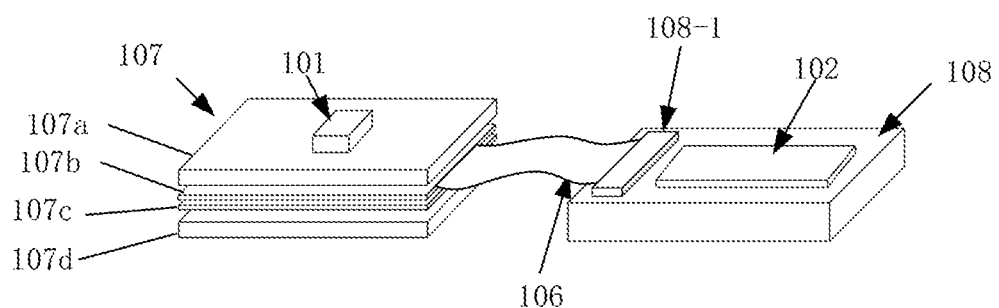
FIG. 5 is a schematic structural diagram of a biological feature detection apparatus according to the fifth embodiment of the present application.

FIG. 5 is a schematic structural diagram of a biological feature detection apparatus according to the fifth embodiment of the present application. As illustrated in FIG. 5, relative to the embodiment illustrated in FIG. 4, in this embodiment, one end of the flexible member 106 is selectively laminated to the first substrate 107, such that one end of the flexible member 106 is embedded into the first substrate 107; and the other end of the flexible member 106 is connected to the first substrate via the second plug 108-1. Accordingly, the first substrate 107 may be a flexible-hard hybrid board, and the second substrate 108 is a hard substrate.

Description is given by using the case where the first substrate 107 is a four-layer structure as an example, that is, the first substrate 107 includes four layers from top to bottom: a first layer PCB 107a, a second layer PCB 107b, a third layer PCB 107c and a fourth layer PCB 107d. The second layer PCB 107b and the third layer PCB 107c correspond to the double-layer structure in the flexible structure 106. In addition, one end of the flexible member 106 is sandwiched between the first layer PCB 107a and the fourth layer PCB 107d in the first substrate 107, and the other end of the flexible member 106 is connected to the second substrate 108 via the second plug 108-1.

It should be noted that in the above embodiment, the numbers of the structure layers of the first substrate 107 and the second substrate 108 in the embodiments stated above are only exemplary, and in practice, the first substrate 107 and the second substrate 108 may also have a 6-layer structure or 8-layer structure.

In addition, reference may also be made to the embodiment illustrate din FIG. 5, or made to the manner of embedding the flexible member into the first substrate. One end of the flexible member in FIG. 5 is connected to the first substrate via a plug, and the other end of the flexible member is embedded into the second substrate.

It should be noted that the above lamination treatment is merely one optional way for embedding the flexible member into the first substrate, and a person skilled in the art would employ other alternative ways under teaching given by the present application.

Nevertheless, in another embodiment, if the first substrate and the second substrate are both substrates having a multilayer structure, any layer in the multilayer structure of the first substrate is made of a flexible material and extends outside to the second substrate and connected to any layer in the multilayer structure of the second substrate; or any layer in the multilayer structure of the second substrate is made of a flexible material and extends outside to the first substrate and connected to any layer in the multilayer structure of the first substrate, such that at least one of the adjustable relative position and relative angle is defined between the light emitting unit and the light receiving unit.

Figure 6:
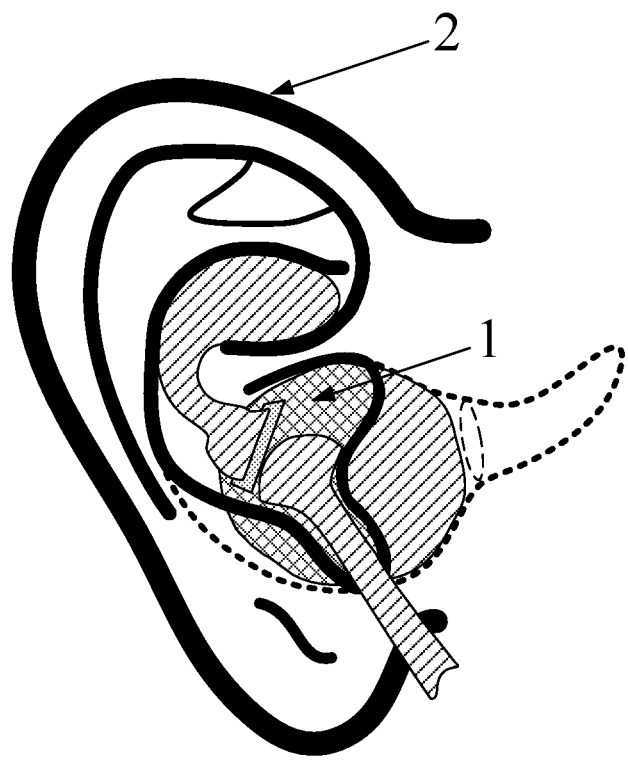
FIG. 6 is a schematic structural diagram of a biological feature detection apparatus according to the sixth embodiment of the present application.

FIG. 6 is a schematic structural diagram of a biological feature detection apparatus according to the sixth embodiment of the present application. In this embodiment, a biological feature detection apparatus 1 is practiced in the form of an earphone, which may also be understood as integrating the biological feature detection apparatus on an earphone structure. For clear description of application of the biological feature detection apparatus, FIG. 6 also illustratively shows an ear 2 as the biological tissue. If the biological feature detection is practiced by using the earphone structure, a position relationship between the light emitting unit and the light receiving unit, and the detection surface on the ear is as described in the embodiments hereinafter. When the detection surface is at the following positions, few modifications are made to the structure of the traditional earphone, and the earphone may be comfortably worn.

Figure 7:
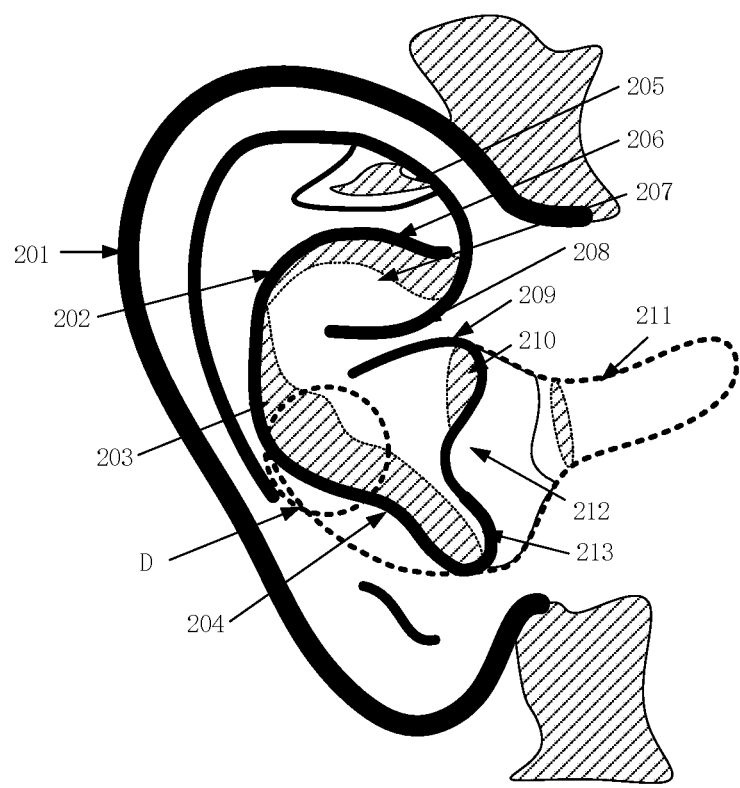
FIG. 7 is a schematic diagram of candidate regions of a detection surface of an ear according to the seventh embodiment of the present application.

FIG. 7 is a schematic diagram of candidate regions of a detection surface of an ear according to the seventh embodiment of the present application. As illustrated in FIG. 2, corresponding to FIG. 6, a portion of the features of the ear 2 include: a helix 201, an antihelix 202, an auricular concha 203, an antitragus 204, a triangular fossa 205, an inferior crus of antihelix 206, a cimba concha 207, a crus of helix 208, a supratragic notch 209, an outer ear canal entrance 210, an ear canal 211, a tragus 212, and an intertragic notch 213.

In the embodiments hereinafter, description is given by using the scenario where the biological feature detection apparatus is practiced with the earphone as a specific product. To better determine the detection surface in a feature region of the ear as illustrated in FIG. 7, after the arterial branches, the vein branches and flatness of different feature regions of the ear are comprehensively analyzed, and a relatively flat feature region where the arterial branch density and the vein branch density are great is used as the detection surface.

Accordingly, in the embodiments hereinafter, exemplarily, the light emitting unit and/or the light receiving unit are arranged in an inner side region of the tragus 211, or in a connection line between the intertragic notch 212 and the outer ear canal entrance 210, a concha cavity region of the auricular concha 203, a region extending to the supratragic notch 209, a region between the inferior crus of antihelix 206 (or the antihelix 202) and the crus of helix 208, a region of the auricular concha 203, a region of the cimba concha 207, a region of the earlobe (not illustrated in the drawings); or the light emitting unit and/or the light receiving unit is arranged in a region enclosed by the crus of helix, the ear canal entrance and the antihelix close to the antitragus. For different users, these regions are morphologically stable. That is, the biological feature detection apparatus has good compatibility with regard to the ears of different users, such that a detection signal having a high signal-to-noise ratio may be simply generated, and accuracy of biological feature detection is ensured.

In a specific embodiment, the light emitting unit and the light receiving unit are arranged in a region D enclosed by the crus of helix, the ear canal entrance and the antihelix close to the antitragus; the light emitting unit and the light receiving unit in the biological feature detection apparatus is tightly attached to the detection surface. Since the arterial branches and the vein branches are densely distributed at this position, the obtained original electrical signal has a great signal-to-noise ratio. Therefore, the original electrical signal has a strong anti-interference capability, and thus accuracy of biological feature detection is further ensured. In addition, since different ear shapes are slightly different in the region D, if the biological feature detection apparatus is integrated on an earphone, the earphone is well compatible with the ears. Therefore, the earphone has a wide application range, and thus achieves a high accuracy of signal detection for different users.

Figure 8A:
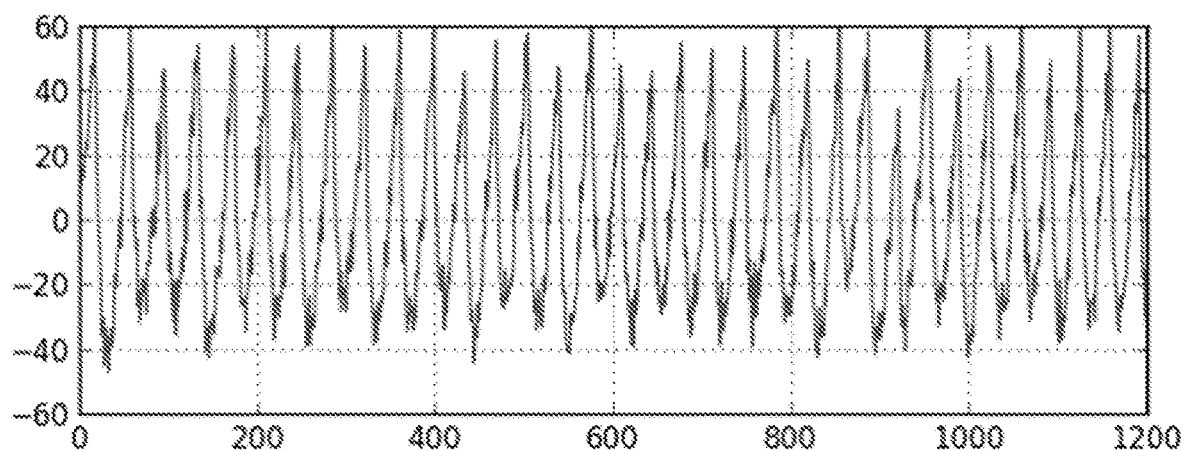
FIG. 8A and FIG. 8B are schematic diagrams before and after a sample detection signal is filtered in a tragus inner-side region according to the eighth embodiment of the present application.
Figure 8B:
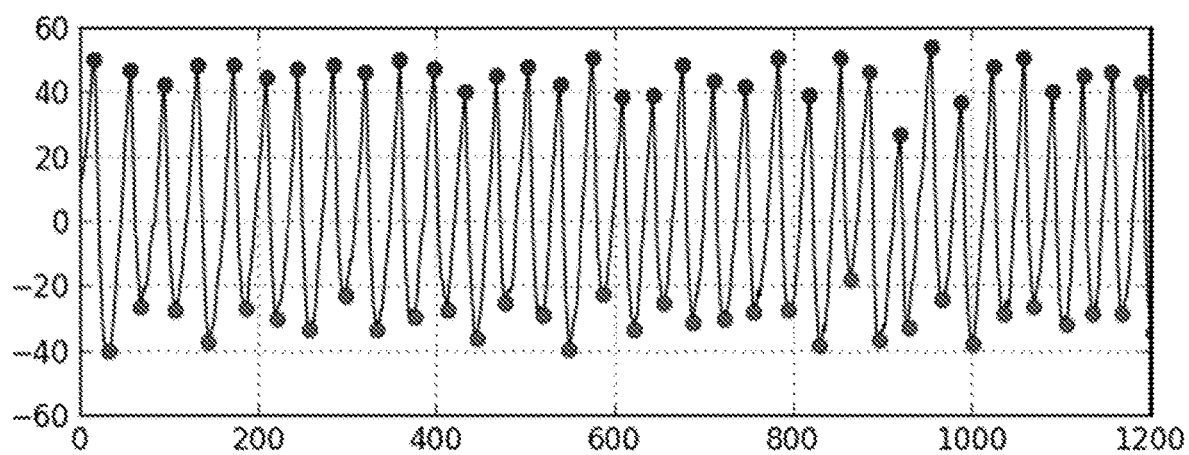

FIG. 8A and FIG. 8B are schematic diagrams before and after a sample original electrical signal in a tragus inner-side region according to the eighth embodiment of the present application. As illustrated in FIG. 8A and FIG. 8B, variations of the original electrical signal are relatively stable, and quality of the electrical signal is high. Accordingly, the arterial branches, the vein branches and the flatness in the inner-side region of the tragus 212 are conditions for determining the detection surface.

Figure 9:
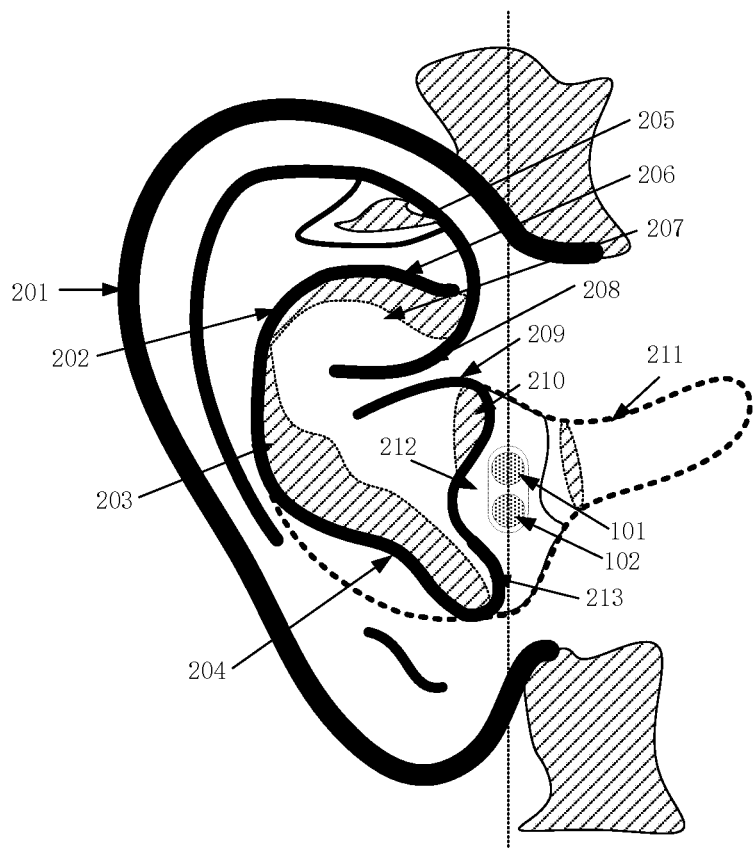
FIG. 9 is a schematic diagram of wearing an earphone on the ear according to the ninth embodiment of the present application.

FIG. 9 is a schematic diagram of wearing an earphone on the ear according to the ninth embodiment of the present application. As illustrated in FIG. 9, in this embodiment, during biological feature detection, the light receiving unit 102 and the light emitting unit 101 are attached to an inner-side region of the tragus 212. Specifically, a reference line R may be defined, and when attaching the light receiving unit 102 and the light emitting unit 101 to the inner-side region of the tragus 212, geometric centers of the light receiving unit 102 and the light emitting unit 101 are located on the reference line R. Since the arterial branches and the vein branches are densely distributed in the inner-side region of the tragus 212 and the flatness is good, the light receiving unit 102 and the light emitting unit 101 may be seamlessly attached to the inner-side region of the tragus 212.

In this embodiment, to enable the light receiving unit 102 and the light emitting unit 101 to be attached to the inner-side region of the tragus 212, the light receiving unit 102 and the light emitting unit 101 may be integrated at a shell attached to the inner-side region of the tragus 212 after the earphone is worn, with no need to arrange an assistance mechanism, such that the biological feature detection apparatus including the light receiving unit 102 and the light emitting unit 101 are integrally tightly attached to the inner-side region of the tragus.

Figure 10:
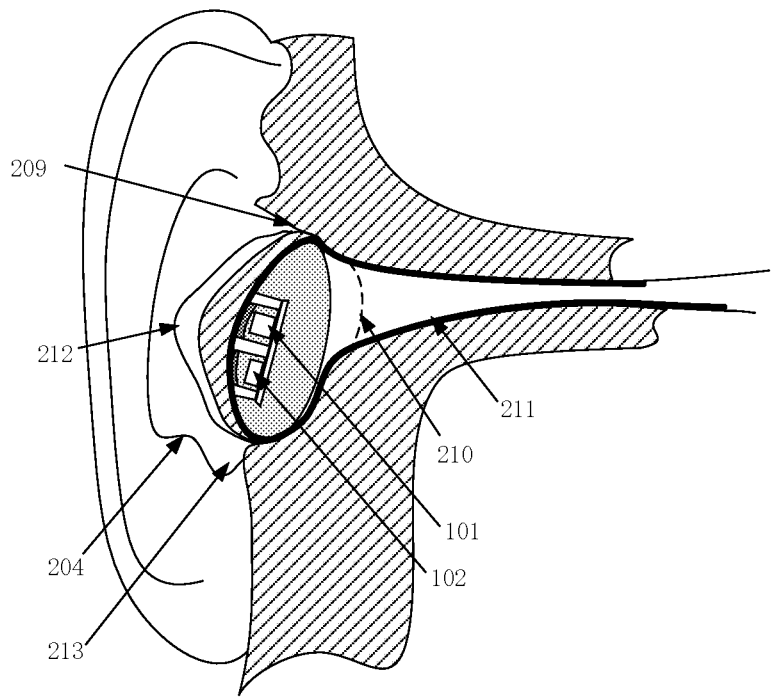
FIG. 10 is a schematic diagram of wearing an earphone on the ear according to the tenth embodiment of the present application.

FIG. 10 is a schematic diagram of wearing an earphone on the ear according to the tenth embodiment of the present application. As illustrated in FIG. 10, in this embodiment, like the ninth embodiment illustrated in FIG. 9, although during biological feature detection, the light receiving unit 102 and the light emitting unit 101 are attached to the inner-side region of the tragus, the specific position to which the receiving unit 102 and the light emitting unit 101 are attached in the inner-side region of the tragus 212 is distal from the outer ear canal entrance. Since the arterial branches and the vein branches are densely distributed in the inner-side region of the tragus 212, and the flatness is good, the light receiving unit 102 and the light emitting unit 101 may be seamlessly attached to the inner-side region of the tragus 212.

In this embodiment, similar to the embodiment illustrated in FIG. 9, to enable the light receiving unit 102 and the light emitting unit 101 to be attached to the inner-side region of the tragus 212, the light receiving unit 102 and the light emitting unit 101 may be integrated at a shell attached to the inner-side region of the tragus 212 after the earphone is worn, with no need to arrange an assistance mechanism, such that the biological feature detection apparatus including the light receiving unit 102 and the light emitting unit 101 are integrally tightly attached to the inner-side region of the tragus.

Figure 11:
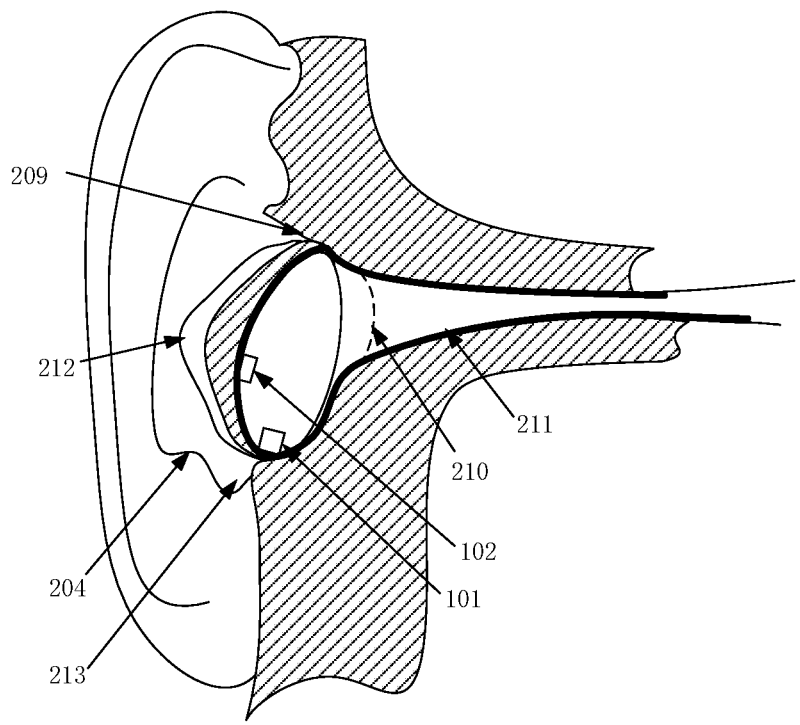
FIG. 11 is a schematic diagram of wearing an earphone on the ear according to the eleventh embodiment of the present application.

FIG. 11 is a schematic diagram of wearing an earphone on the ear according to the eleventh embodiment of the present application. As illustrated in FIG. 11, in this embodiment, like the embodiment illustrated in FIG. 9, during biological feature detection, the light receiving unit 102 is attached to the inner-side region of the tragus, and the light emitting unit 101 is further located in a connection region between the intertragic notch and the outer ear cannel entrance and is also attached to a feature region enclosed by the tragus, the antitragus and the intertragic notch. Since the arterial branches and the vein branches are densely distributed in the inner-side region of the tragus 212 and the connection region between the intertragic notch and the outer ear canal entrance, and the flatness is good, the light receiving unit 102 and the light emitting unit 101 may be seamlessly attached to the ear.

It should be noted that in another embodiment, the light emitting unit 101 is attached to the intertragic notch, and the light receiving unit 102 is further located in the connection region between the intertragic notch and the outer ear canal entrance and is located in the feature region enclosed by the tragus, the antitragus and the intertragic notch.

In this embodiment, similar to the embodiment illustrated in FIG. 9, to enable the light receiving unit 102 and the light emitting unit 101 to be tightly attached to the inner-side region of the tragus 212 and the connection region between the intertragic notch and the outer ear canal entrance, the light receiving unit 102 and the light emitting unit 101 may be integrated at a shell attached to the inner-side region of the tragus 212 and at a shell attached to the connection region between the intertragic notch and the outer ear canal entrance after the earphone is worn, with no need to arrange an assistance mechanism, such that the biological feature detection apparatus including the light receiving unit 102 and the light emitting unit 101 are integrally tightly attached to ear.

Figure 12:
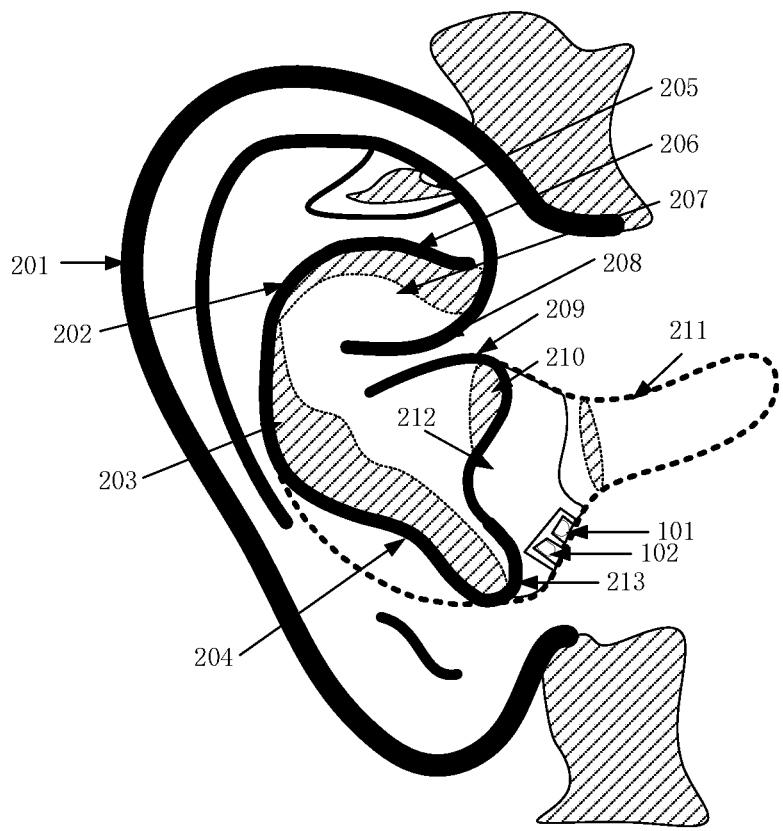
FIG. 12 is a schematic diagram of wearing an earphone on the ear according to the twelfth embodiment of the present application.

FIG. 12 is a schematic diagram of wearing an earphone on the ear according to the twelfth embodiment of the present application. As illustrated in FIG. 12, in this embodiment, the light emitting unit 101 and the light receiving unit 102 are both located in the connection region between the intertragic notch and the outer ear canal entrance, and are also located in the feature region enclosed by the tragus, the antitragus and the intertragic notch.

In this embodiment, similar to the embodiment illustrated in FIG. 12, to enable the light receiving unit 102 and the light emitting unit 101 to be tightly attached to the connection region between the intertragic notch and the outer ear canal entrance, the light receiving unit 102 and the light emitting unit 101 may be integrated at a shell attached to the connection region between the intertragic notch and the outer ear canal entrance after the earphone is worn, with no need to arrange an assistance mechanism, such that the biological feature detection apparatus including the light receiving unit 102 and the light emitting unit 101 are integrally tightly attached to the inner-side region of the tragus.

Figure 13:
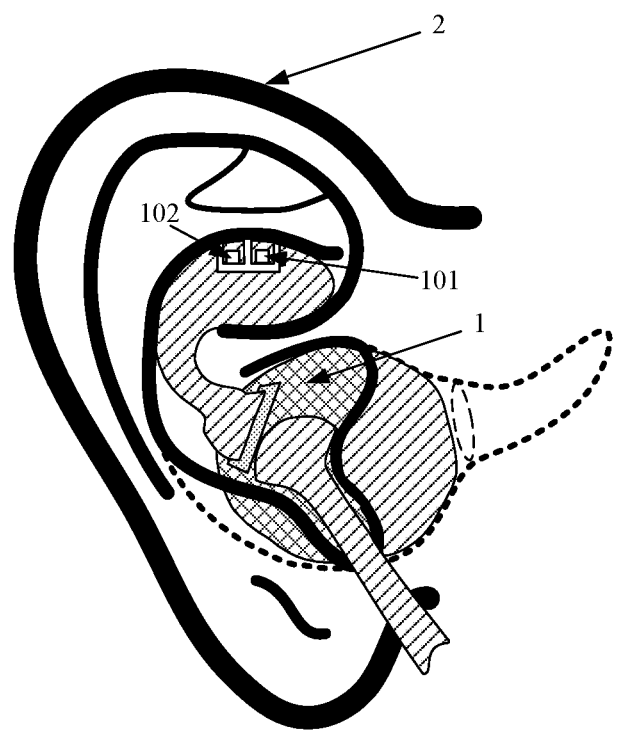
FIG. 13 is a schematic diagram of wearing an earphone on the ear according to the thirteenth embodiment of the present application.

FIG. 13 is a schematic diagram of wearing an earphone on the ear according to the thirteenth embodiment of the present application. As illustrated in FIG. 13, the light receiving unit 102 and the light emitting unit 101 are attached to a region between the inferior crus of antihelix and the crus of helix.

In this embodiment, the earphone may further include: a wearing assistance mechanism 110. The light receiving unit 102 and the light emitting unit 101 are arranged on the wearing assistance mechanism 101, such that the light receiving unit 102 and the light emitting unit 101 are attached to the region between the inferior crus of antihelix and the crus of helix.

In another embodiment, as illustrated in FIG. 13, the light receiving unit 102 and the light emitting unit 101 are attached to a region between the antihelix and the crus of helix.

In another embodiment, the wearing assistance mechanism 110 may also be detached from the earphone, such that the wearing assistance mechanism 110 is assembled to the earphone where biological feature detection is desired, and is detached from the earphone where biological feature detection is not desired. In this way, the earphone and the wearing assistance mechanism 110 may flexibly cooperate with each other.

During practice, one end of the wearing assistance mechanism 110 may be fixed to the shell of the earphone, and the other end of the wearing assistance mechanism 110 is connected to the light receiving unit 102 and the light emitting unit 101.

Figure 14:
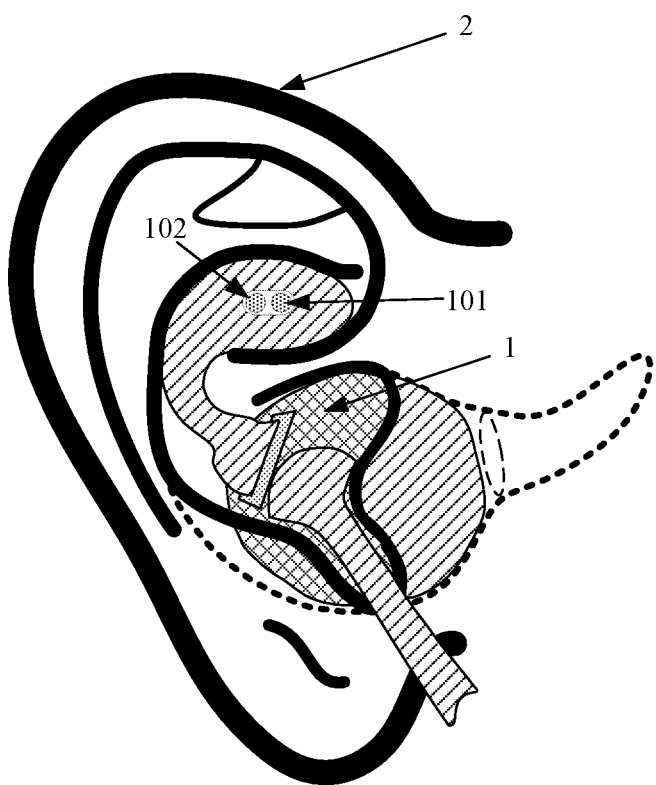
FIG. 14 is a schematic diagram of wearing an earphone on the ear according to the fourteenth embodiment of the present application.

FIG. 14 is a schematic diagram of wearing an earphone on the ear according to the fourteenth embodiment of the present application. As illustrated in FIG. 14, in this embodiment, the light receiving unit 102 and the light emitting unit 101 are both attached to a region of the cimba concha; in another embodiment, either the light receiving unit 102 or the light emitting unit 101 is attached to the region of the cimba concha.

In the embodiments illustrated in FIG. 9 to FIG. 14, biological feature detection is carried out based on the light reflection theory. However, it should be noted that the position of the light receiving unit 102 or the light emitting unit 101 may be correspondingly adjusted to carry out biological feature detection based on the light projection theory.

In another embodiment, the light receiving unit 102 is attached to the region of the cimba concha, and the light emitting unit 101 is attached to a behind-the-ear region corresponding to the region of the cimba concha. Accordingly, biological feature detection may be carried out based on the light projection theory.

Figure 15:
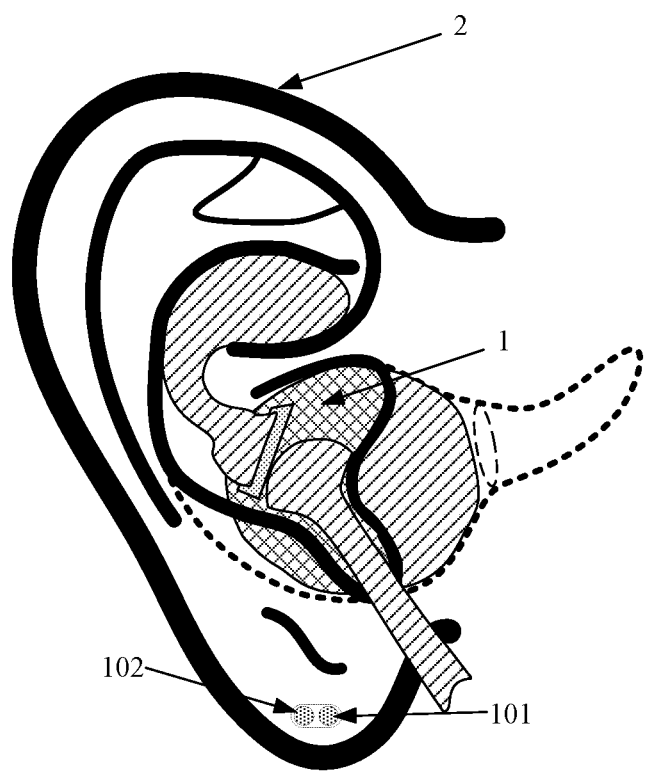
FIG. 15 is a schematic diagram of wearing an earphone on the ear according to the fifteenth embodiment of the present application.

FIG. 15 is a schematic diagram of wearing an earphone on the ear according to the fifteenth embodiment of the present application. As illustrated in FIG. 15, the light receiving unit 102 and the light emitting unit 101 are both attached to a region of the earlobe. In this embodiment, the light receiving unit 102 and the light emitting unit 101 are arranged on the same side of the region of the earlobe. Accordingly, biological feature detection may be carried out based on the light projection theory.

Figure 16:
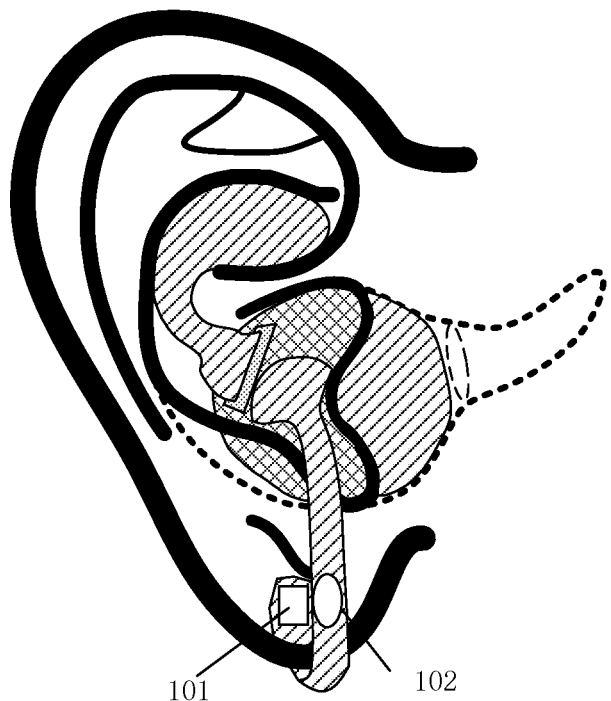
FIG. 16 is a schematic diagram of wearing an earphone on the ear according to the sixteenth embodiment of the present application.

In addition, if the light receiving unit 102 and the light emitting unit 101 are respectively arranged on two sides of the region of the earlobe, biological feature detection may be correspondingly carried out based on the light projection theory. Referring to FIG. 16, a schematic diagram of wearing an earphone on the ear according to the sixteenth embodiment of the present application is given.

Figure 17:
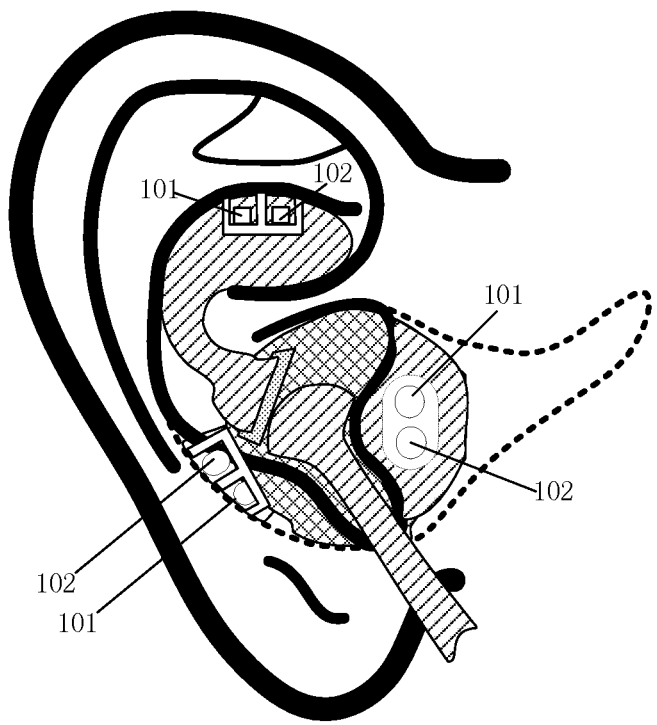
FIG. 17 is a schematic diagram of wearing an earphone on the ear according to the seventeenth embodiment of the present application.

FIG. 17 is a schematic diagram of wearing an earphone on the ear according to the seventeenth embodiment of the present application. As illustrated in FIG. 17, different from the above embodiment, three pairs of light emitting units 101 and light receiving units 102 are arranged on the earphone. Specifically, as illustrated in FIG. 17, three pairs of light emitting unit 101 and light receiving unit 102 are respectively arranged in the inner-side region of the tragus, in the region between the inferior crus of helix and the crus of helix and in the region of the concha cavity.

Figure 18:
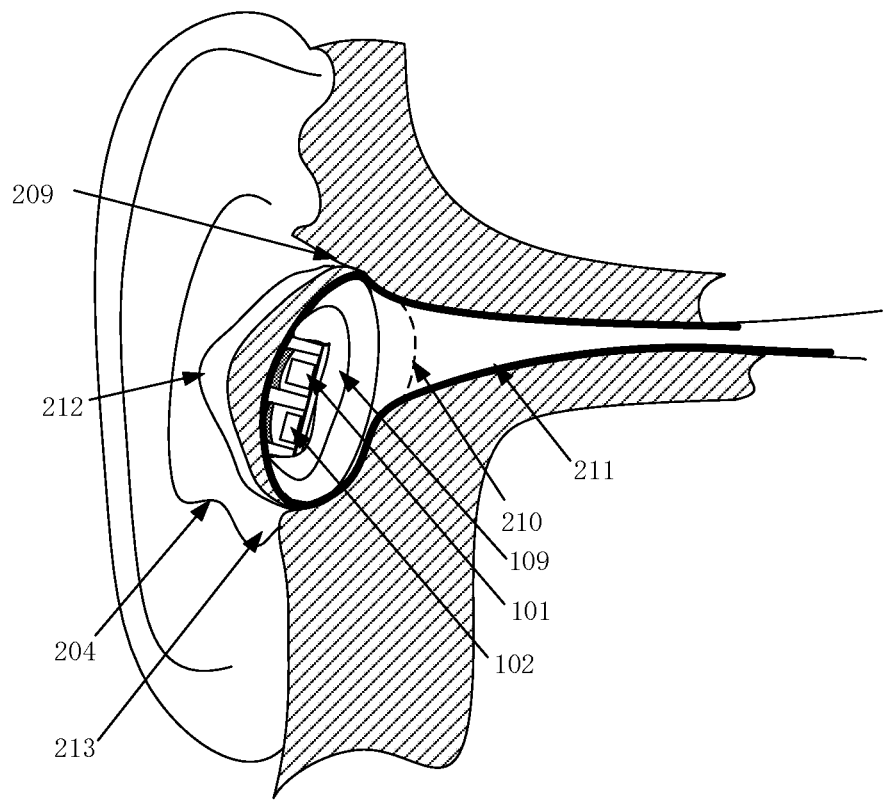
FIG. 18 is a schematic diagram of wearing an earphone on the ear according to the eighteenth embodiment of the present application.

FIG. 18 is a schematic diagram of wearing an earphone on the ear according to the eighteenth embodiment of the present application. As illustrated in FIG. 18, in this embodiment, an elastic unit 109 is additionally arranged. During biological feature detection, the elastic unit 109 enables the light emitting unit 101 and the light receiving unit 102 to be tightly attached to the detection surface of the ear. In this embodiment, using the scenario where an elastic unit is added based on the embodiment illustrated in FIG. 8 as an example, as illustrated in FIG. 18, the elastic unit 109 is arranged in a peripheral region of the ear distal from the outer ear canal entrance, such that the light emitting unit 101 and the light receiving unit 102 are pressed and thus are tightly attached to the detection surface of the ear.

Alternatively, in another embodiment, the elastic unit 109 may only press the light emitting unit 101 and the light receiving unit 102, such that the pressed light emitting unit 101 or the pressed light receiving unit 102 is tightly attached to the detection surface of the ear.

In the embodiment including the elastic unit 109, even in the movement, the light emitting unit 101 and/or the light receiving unit 102 may still be tightly attached to the detection surface of the ear. This may prevent the biological feature detection apparatus from sliding relative to the detection surface, such that stability and strength of the detection signal are improved. In addition, this also mitigates or eliminates adverse impacts caused by the movement to the signal-to-noise ratio of the detection signal, and further improves the signal-to-noise ratio of the original electrical signal.

In the above embodiment, the elastic unit 109 may be made of a soft silicone material. The elastic unit 109 may be specifically arranged inside the shell of the earphone.

Figure 19:
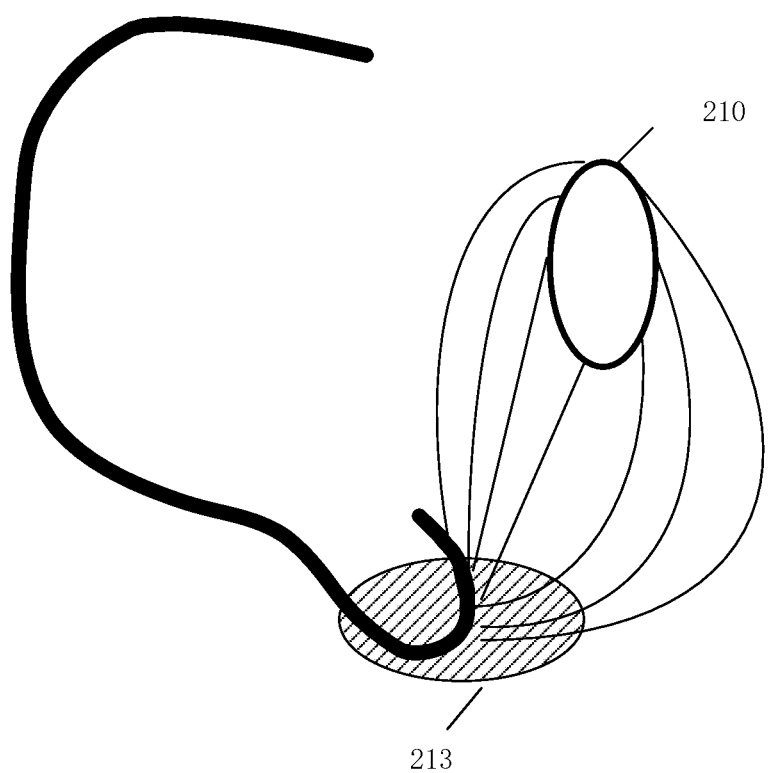
FIG. 19 is a schematic diagram of a connection line between an intertragic notch and an outer ear canal entrance according to the nineteenth embodiment of the present application.

FIG. 19 is a schematic diagram of a connection region between an intertragic notch and an outer ear canal entrance according to the nineteenth embodiment of the present application. As illustrated in FIG. 19, a plurality of connection lines are presented in the connection region between the intertragic notch and the outer ear canal entrance, which is also referred to as formation of a connection cluster. During arrangement of the light emitting unit or the light receiving unit, the light emitting unit or the light receiving unit may be specifically arranged on any connection line in the connection cluster.

In the above embodiment, the light emitter may be specifically practiced by an LED lamp or a LED tube, and the light receiver may be specifically practiced by a photodiode.

The above described device embodiments are merely for illustration purpose only. The modules which are described as separate components may be physically separated or may be not physically separated, and the components which are illustrated as modules may be or may not be physical modules, that is, the components may be located in the same position or may be distributed into a plurality of network modules. A part or all of the modules may be selected according to the actual needs to achieve the objectives of the technical solutions of the embodiments. Persons of ordinary skill in the art may understand and implement the present application without paying any creative effort.

Although the preferred embodiments of the present application are described above, once knowing the basic creative concept, a person skilled in the art can make other modifications and variations to these embodiments. Therefore, the appended claims are intended to be construed as covering the preferred embodiments and all the modifications and variations falling within the scope of the present application. Obviously, a person skilled in the art can make various modifications and variations to the present application without departing from the spirit and scope of the present application. In this way, the present application is intended to cover the modifications and variations if they fall within the scope of the appended claims of the present application and equivalent technologies thereof.

What is claimed is:

1. A biological feature detection apparatus, comprising:
a light emitting unit and a light receiving unit, wherein the light emitting unit is configured to emit light to a detection surface of an ear, the light emitted by the light emitting unit is processed by the ear and then transmitted to the light receiving unit, the light receiving unit is configured to receive the light and perform a photoelectric conversion to generate an original electrical signal for biological feature detection, and the light emitting unit and light receiving unit are in close proximity and insertable in the ear;
a first substrate, a second substrate and a flexible member, wherein the light emitting unit is arranged on the first substrate, the light receiving unit is arranged on the second substrate, the first substrate and the second substrate are connected via the flexible member, and the flexible member is configured to permit adjustment of a relative position and a relative angle between the light emitting unit and the light receiving unit;
an optical shielding unit and a light guiding unit, wherein the light guiding unit is configured to form enclosures around the light emitting unit and the light receiving unit, and the optical shielding unit is configured to form enclosures around the light emitting unit and the light receiving unit such that the light guiding unit is configured to guide the light emitted by the light emitting unit to the detection surface of the ear and guide the light being processed by the ear to the light receiving unit, and the optical shielding unit is configured to shield or absorb the light emitted by the light emitting unit to prevent the light emitted by the light emitting unit from being directly transmitted to the light receiving unit without being processed by the ear.

2. The biological feature detection apparatus according to claim 1, wherein the flexible member is connected to the first substrate and the second substrate respectively via a solder pad or a plug.

3. The biological feature detection apparatus according to claim 1, wherein the first substrate and the second substrate have multilayer structures respectively; and at least one end of the flexible member is embedded into the multilayer structures of the first substrate or the second substrate to be connected to the first substrate or the second substrate respectively.

4. The biological feature detection apparatus according to claim 1, wherein the first substrate and the second substrate have multilayer structures respectively; wherein any layer in the multilayer structure of the first substrate is made of a flexible material and extends outside to the second substrate and connected to any layer in the multilayer structure of the second substrate; or any layer in the multilayer structure of the second substrate is made of a flexible material and extends outside to the first substrate and connected to any layer in the multilayer structure of the first substrate, and the flexible member comprises the flexible material and its extension.

5. The biological feature detection apparatus according to claim 1, wherein the detection apparatus comprises both the optical shielding unit and the light guiding unit, and the optical shielding unit and the light guiding unit are integrally arranged, or the optical shielding unit and the light guiding unit are separately arranged.

6. The biological feature detection apparatus according to claim 1, wherein the light emitting unit and the light receiving unit are both provided with the light guiding unit; wherein the light guiding unit on the light emitting unit and the light guiding unit on the light receiving unit are integrally arranged or separately arranged.

7. The biological feature detection apparatus according to claim 1, further comprising a processing circuit and a control circuit, wherein:
the processing circuit is configured to perform an analog-to-digital conversion for the original electrical signal to generate a digital signal and filter the digital signal; and
the control circuit is configured to control the light emitting unit to emit light to the ear.

8. The biological feature detection apparatus according to claim 1, further comprising a processor; wherein the processor is configured to perform biological feature detection based on the original electrical signal.

9. The biological feature detection apparatus according to claim 1, wherein the relative position is a linear distance between a geometric center of the light emitting unit and a geometric center of the light receiving unit, and the relative angle is a normal angle between a planar surface of the light emitting unit and a planar surface of the light receiving unit.

10. The biological feature detection apparatus according to claim 1, wherein the biological feature is a heart rate feature or a blood oxygen feature based on a photoplethysmogram signal.

11. The biological feature detection apparatus according to claim 1, wherein the light receiving unit and the light emitting unit are attached to a tragus inner-side region of the ear the light receiving unit and the light emitting unit are located in a concha cavity of the ear; or the light receiving unit and the light emitting unit are located in a region enclosed by a crus of helix of the ear, an ear canal entrance and a antihelix close to an antitragus of the ear.

12. The biological feature detection apparatus according to claim 11, wherein:
when the light receiving unit is attached to the tragus inner-side region, the light emitting unit is located in an underneath connection region between an intertragic notch and an outer ear canal entrance; or
when the light emitting unit is attached to the tragus inner-side region, the light receiving unit is located in an underneath connection region between an intertragic notch and an outer ear canal entrance.

13. The biological feature detection apparatus according to claim 11, further comprising a wearing assistance mechanism; wherein the light receiving unit and the light emitting unit are arranged on the wearing assistance mechanism, such that the light receiving unit and the light emitting unit are arranged in the region between the inferior crus of antihelix and the crus of helix or in the region between the antihelix and the crus of helix.

14. The biological feature detection apparatus according to claim 1, further comprising an elastic unit; wherein, during biological feature detection, the elastic unit is configured to enable the light emitting and/or the light receiving unit to be tightly attached to the ear.

15. The biological feature detection apparatus according to claim 1, wherein the light guiding unit has a surface shape conformed to a shape of the detection surface of the ear.

16. The biological feature detection apparatus according to claim 1, wherein the light shielding unit has a surface shape conformed to a shape of the detection surface of the ear.

17. An electronic terminal, comprising a biological feature detection apparatus, wherein the biological feature detection apparatus comprising:
  a light emitting unit and a light receiving unit, wherein the light emitting unit is configured to emit light to a detection surface of an ear, the light emitted by the light emitting unit is processed by the ear and then transmitted to the light receiving unit, and the light receiving unit is configured to receive the light and perform a photoelectric conversion to generate an original electrical signal for biological feature detection,
  a first substrate, a second substrate and a flexible member, wherein the light emitting unit is arranged on the first substrate, the light receiving unit is arranged on the second substrate, the first substrate and the second substrate are connected via the flexible member, and the flexible member is configured to permit adjustment of a relative position and a relative angle between the light emitting unit and the light receiving unit, and the light emitting unit and light receiving unit are in close proximity and insertable in the ear;
  an optical shielding unit and a light guiding unit, wherein the light guiding unit is configured to form enclosures around the light emitting unit and the light receiving unit, and the optical shielding unit is configured to form enclosures around the light emitting unit and the light receiving unit such that the light guiding unit is configured to guide the light emitted by the light emitting unit to the detection surface of the ear and guide the light being processed by the ear to the light receiving unit, and the optical shielding unit is configured to shield or absorb the light emitted by the light emitting unit to prevent the light emitted by the light emitting unit from being directly transmitted to the light receiving unit without being processed by the ear.

* * * * *